(12) United States Patent
Watschke (10) Patent No.: US 9,061,125 B2
(45) Date of Patent: Jun. 23, 2015

(54) BLADDER DRUG ELUTING DEVICE

(71) Applicant: AMS Research Corporation, Minnetonka, MN (US)

(72) Inventor: Brian P. Watschke, Minneapolis, MN (US)

(73) Assignee: AMS Research Corporation, Minnetonka, MN (US)

( * ) Notice: Subject to any disclaimer, the term of this patent is extended or adjusted under 35 U.S.C. 154(b) by 125 days.

(21) Appl. No.: 13/741,918

(22) Filed: Jan. 15, 2013

(65) Prior Publication Data

US 2013/0253476 A1    Sep. 26, 2013

Related U.S. Application Data

(60) Provisional application No. 61/613,777, filed on Mar. 21, 2012.

(51) Int. Cl.
| A61M 25/10 | (2013.01) |
| A61M 29/00 | (2006.01) |
| A61M 31/00 | (2006.01) |

(52) U.S. Cl.
CPC ............... *A61M 25/10* (2013.01); *A61M 29/00* (2013.01); *A61M 31/002* (2013.01); *A61M 2025/105* (2013.01); *A61M 2025/1054* (2013.01)

(58) Field of Classification Search
CPC ................ A61M 25/10; A61M 29/00; A61M 2025/105; A61M 2025/1054; A61M 31/002
USPC .................. 604/517, 96.01, 100.1, 103.1, 604/103.06–103.08, 523, 544
See application file for complete search history.

(56) References Cited

U.S. PATENT DOCUMENTS

| 5,007,897 | A | 4/1991 | Kalb |
| 5,681,281 | A | 10/1997 | Vigil |
| 5,746,716 | A | 5/1998 | Vigil |
| 6,338,726 | B1 * | 1/2002 | Edwards et al. .......... 604/101.03 |
| 7,837,670 | B2 | 11/2010 | Barath |
| 8,439,867 | B2 * | 5/2013 | Staskin ..................... 604/103.01 |
| 8,460,240 | B2 * | 6/2013 | Towler ...................... 604/103.07 |
| 2004/0064094 | A1 | 4/2004 | Freyman |
| 2004/0175408 | A1 | 9/2004 | Chun |
| 2007/0135803 | A1 | 6/2007 | Belson |
| 2013/0060229 | A1 * | 3/2013 | Herman et al. ................ 604/506 |

* cited by examiner

*Primary Examiner* — Rebecca E Eisenberg
(74) *Attorney, Agent, or Firm* — Kagan Binder, PLLC (57) ABSTRACT

A drug delivery system that can be deployed from a catheter and retained within the bladder for delivery of treatment drug solutions over a period of time. The delivery system includes an inflatable or expandable delivery element that can be collapsed within the catheter tip for navigation into the bladder before being inflated or expanded within the bladder. The inflated or expanded delivery element can engage the bladder walls or sized to be too large to be passed from the bladder such that the delivery element is retained within the bladder after inflation or expansion to administer a treatment drug solution over an extended period of time.

19 Claims, 7 Drawing Sheets

Treatment drug solution

BLADDER DRUG ELUTING DEVICE

RELATED APPLICATION

The present application claims the benefit of U.S. Provisional Application No. 61/613,777 entitled BLADDER DRUG ELUTING DEVICE and filed Mar. 21, 2012, which is incorporated herein in its entirety by reference.

FIELD OF THE INVENTION

The present invention is generally directed to a drug elution device positionable within the bladder for prolonged delivery of treatment drugs. Specifically, the present invention is directed to a drug eluting device that can be collapsed for transport through a biological lumen to bladder before being expanded to retain the drug eluting device within the bladder.

BACKGROUND OF THE INVENTION

The bladder is a hollow organ for receiving and storing urine produced during digestion before the urine is expelled from the body. The chemical conditions within the bladder, such as the pH, are constantly changing with the influx of new urine and expelling of urine from the bladder. The chemical characteristics of the urine itself are also constantly changing depending on the individual's recent meals, overall diet, timing between meals, present hydration, acute and chronic health conditions, and a plurality of other factors. The characteristics can change dramatically on a daily or even hourly basis. The constantly changing chemical characteristics of the bladder can make effectively delivering chemical drugs to the bladder difficult. In particular, effective long term drug treatments for the bladder are particularly challenging.

Treatment drugs are typically administered to the bladder by navigating a catheter through the urethra until and end of the catheter is positioned within the bladder. The treatment drug is then supplied via the lumen defined by the catheter and expelled within the bladder. If the chemical conditions within the bladder are not optimal when the drugs are administered, the drugs may not sufficiently dissolve to cover a sufficient area or diffuse over too great an area to effectively treat the disorder. In particular, if the pH of the urine is outside a predetermined range, the treatment drug could have little to no effect. The problem is further exaggerated with treatment drugs that are administered within the bladder in a form designed to be gradually administered over time such as time release drug capsules or ampules. The changing bladder conditions and constantly refreshing urine can cause the drugs to be administered either too quickly or too slowly, thereby preventing effective delivery of the drugs.

Presently, the effectiveness of the drug administration process in the bladder is improved by doubling the concentration of the drug to overcome unfavorable conditions or by combining the treatment drugs with a buffering solution to effectively create the desired conditions for a period of time. Although these approaches can improve the efficacy of long term drug treatments to the bladder, these approaches are not without significant drawbacks. Increasing the concentration of the drugs that are initially delivered reduces the likelihood that the dosages that are administered will be insufficient. However, the increased concentration also creates a possibility of an overdose in treatment drugs, which can lead to significant complications. Similarly, the buffering solution is an added chemical solution that can create side effects leading to additional complications for the patient. Long term administration of the drugs can further exaggerate the inherent drawbacks of these treatment methods.

The inability to consistently and effectively administer treatment drugs to the bladder over a long period of time can prevent effective treatment of certain disorders, such as cancer. As such, there is a need for a means of effective long term and consistent drug delivery within a bladder.

SUMMARY OF THE INVENTION

The present invention is generally directed to a drug delivery system that can be deployed from a catheter and retained within the bladder for administering treatment drug solutions over a period of time. The delivery system generally comprises an inflatable or expandable delivery element that can be collapsed within the catheter tip and inflated or expanded after the catheter tip is navigated into the bladder. The inflated or expanded delivery element can engage the bladder walls or sized to be too large to be passed from the bladder such that the delivery element is retained within the bladder after inflation or expansion to administer a treatment drug solution over an extended period of time. Alternatively, the treatment drug can be delivered to the delivery element with a jet injection system at higher pressure to facilitate more rapid introduction of the treatment drug into bladder tissue.

In one aspect, the delivery element can define an internal space for containing a drug treatment solution with a semi-permeable exterior through which the drug treatment solution diffuse over an extended period of time. The exterior prevents complete intermixing of the drug treatment solution with the urine during the initial treatment and instead permits gradual administration of the drug treatment solution at an effective dosage over a period of time. The exterior also limits the effect of changing bladder conditions on the efficacy of the treatment drugs. In another aspect, the exterior comprises a degradable material adapted to dissolve or degrade over a predetermined period of time to gradually release the drug treatment solution. In yet another aspect, the delivery element can comprise at least one orifice through which the drug treatment solution slowly elutes through over an extended period of time.

A drug delivery system, according to a representative embodiment of the present invention, can comprise a delivery element and a catheter having a tip for receiving and deploying the delivery element, wherein the delivery element comprises an inflatable balloon. The inflatable balloon can further comprise a balloon exterior defining an interior space for receiving a treatment drug solution. In one aspect, the catheter can comprise a lumen for administering the drug solution into the interior space of the balloon to inflate the balloon. In this configuration, the balloon can comprise a sealing interface with the catheter tip such that the balloon can remain inflated in the bladder after the catheter tip separates from the balloon. The bladder exterior can comprise a semi-permeable membrane, a degradable membrane, a plurality of orifices or other means of permitting prolonged elution of the treatment drugs from the interior space of the balloon.

In operation, the catheter can be navigated through the urethra until the tip of the catheter is positioned within the bladder. The treatment drug is then supplied through the catheter lumen to inflate the balloon. The balloon can be shaped to contact the bladder wall once inflated. The treatment drug can then be eluted or forced from the balloon into the bladder wall. In one aspect, the catheter can be separated from the balloon and removed from the body while leaving the inflated balloon in place. Once the treatment drug has been administered, the balloon can be deflated by the original catheter or a second catheter navigated into the bladder in a subsequent procedure. Alternatively, the balloon wall can comprise a degradable material formulated to breakdown after a predetermined time allowing the balloon wall to be passed from the bladder wall. In some embodiments, the treatment drug can be delivered into the balloon at higher pressure for more rapid introduction into the bladder tissue using a jet injection system.

According to a representative embodiment of the present invention, the delivery element can comprise a deployable ring. The ring shape permits the ring to be retained within the bladder while allowing the urine to normally pass through the center of the ring. The edges of the ring are sized to engage the sides of the bladder wall to prevent shifting of the ring following deployment. In one aspect, the ring can comprise a ring exterior defining an interior space for receiving a treatment drug. In this configuration, the ring can be filled with the treatment drug to inflate the ring in a similar manner to the balloon. In another aspect, the ring can comprise a flexible material that unfurls and expands when deployed from the catheter tip. In this configuration, the ring can be impregnated with the treatment drug and coated to provide extended delivery of the treatment drug. Alternatively, the ring can comprise a base material coated or impregnated with the treatment drug. In some embodiments, the treatment drug can be delivered into the deployable ring at higher pressure for more rapid introduction into the bladder tissue using a jet injection system.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The invention can be completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Figure 1:
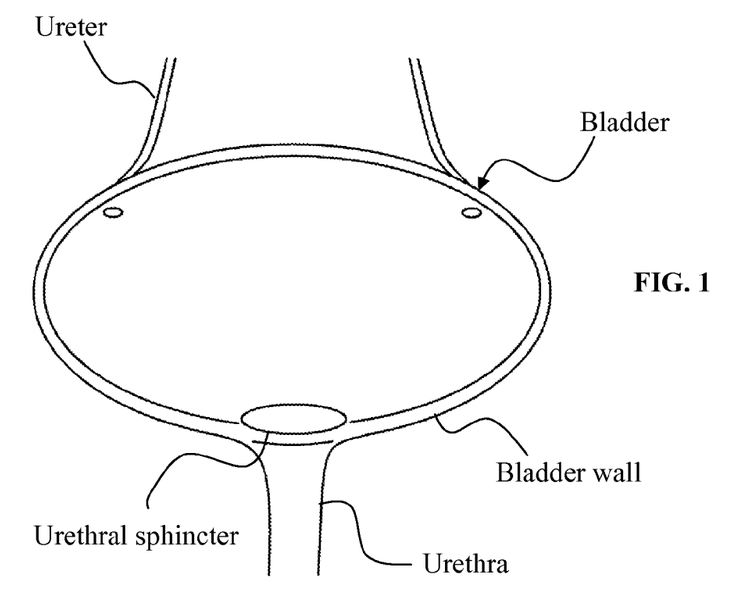
FIG. 1 is a representative schematic view of a bladder.
Figure 2:
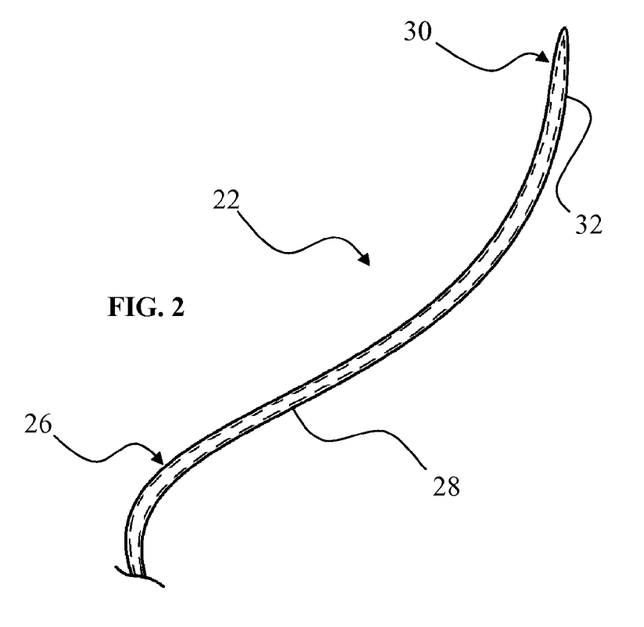
FIG. 2 is a partial perspective cross-sectional view of a catheter of a drug delivery system according to an embodiment of the present invention.
Figure 3:
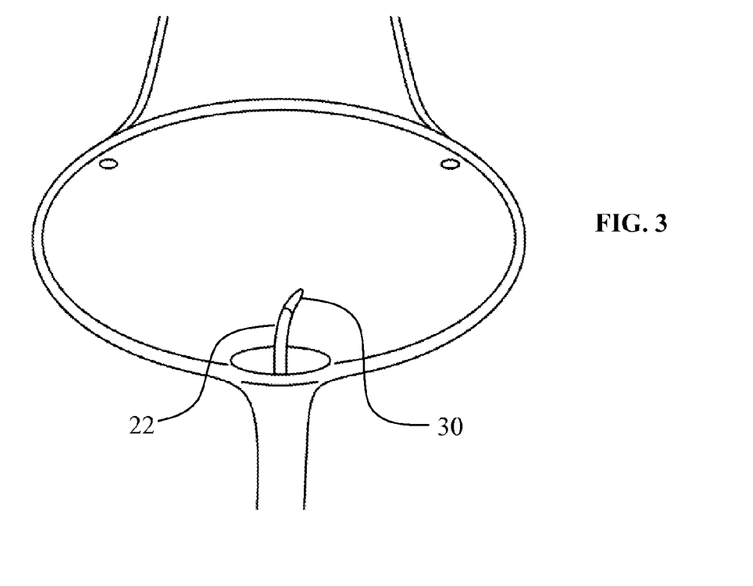
FIG. 3 is a representative cross-sectional schematic view of a bladder illustrating the navigation of a catheter of a drug delivery device through the urethra according to an embodiment of the present invention.

As depicted in FIG. 1, a bladder generally comprises an expandable bladder wall defining an interior space. Two ureters are fluidly connected to the bladder to supply urine into the interior space of the bladder. Similarly, a urethra is fluidly connected to the bladder to expel urine from the bladder. A urethral sphincter controls the flow of urine from the bladder through the urethra. The description of the bladder is not intended to be limiting, but rather to aid in the description of the present invention.

As depicted in FIGS. 2-11, a drug delivery device 20, according to an embodiment of the present invention, can comprise a catheter 22 and a deployable delivery element 24 capable of transitioning between a non-expanded state 23 and an expanded state 25. The catheter 22 comprises an elongated body 26 defining a lumen 28 and a tip 30 at one end of the elongated body 26. The lumen 28 extends the length of the catheter 22 providing fluid communication between one end of the catheter 22 and the opposite end of the catheter 22. In one aspect, the tip 30 defines a tip space 32 for receiving the delivery element 24 in the non-expanded state 23. In this configuration, the catheter 22 can further comprise at least one control wire extendable through the lumen 28 for deploying the delivery element 24 from the tip space 32 through the opposite end of the catheter 22.

Figure 5:
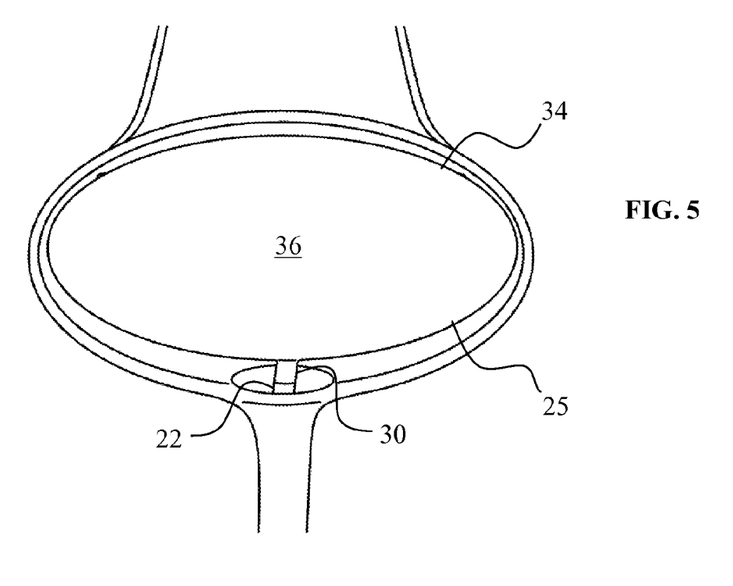
FIG. 5 is a representative cross-sectional side view of a bladder depicting the inflated balloon depicted in FIG. 3.
Figure 6:
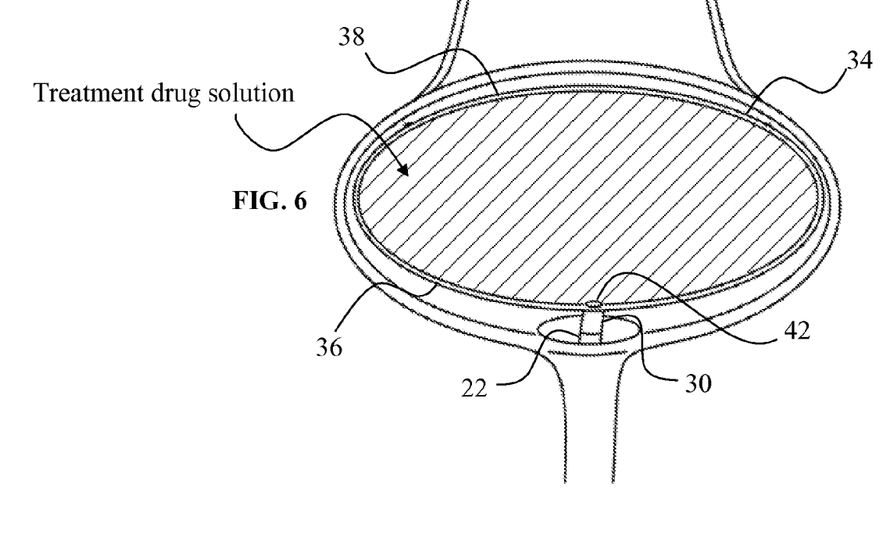
FIG. 6 is a representative cross-sectional side view of a bladder depicting the inflated balloon depicted in FIG. 3.
Figure 7:
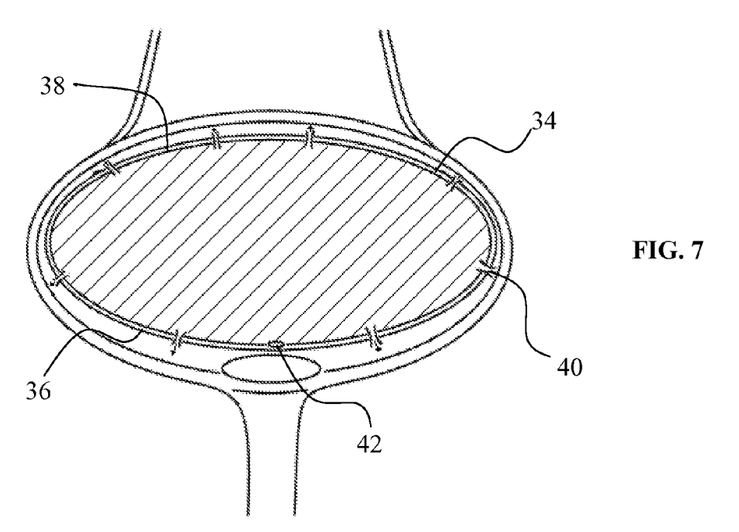
FIG. 7 is a representative cross-sectional side view of a bladder depicting the inflated balloon depicted in FIG. 3 illustrating elution of treatment drugs through a plurality of orifices in the inflated balloon.

As depicted in FIG. 3-8, according to an embodiment of the present invention, the deployable delivery element 24 comprises a balloon 34 having a deflated non-expanded state 23 and an inflated expanded state 25. The balloon 34 further comprises a balloon wall 36 defining an interior space 38 for receiving a drug treatment solution. In one aspect, the balloon wall 36 comprises an elastic material that stretches as the treatment drug is fed into the interior space 38 thereby causing the balloon 34 to transition/inflate into the expanded state 25. Similarly, in one aspect, the balloon wall 36 can comprise a semi-permeable material allowing the treatment drug contained within the interior space 38 to diffuse from the inflated balloon 34 over a prolonged period of time while preventing urine from entering the interior space 38. In another aspect, the balloon wall 36 comprises a degradable material that gradually breaks down over an extended period of time, thereby gradually dispensing the treatment drug contained within the interior space 38 of the balloon 34. In yet another aspect, the bladder wall 36 comprises a plurality of orifices 40, as depicted in FIG. 7, through which the treatment drug solution elutes over a prolonged period of time.

Figure 4:
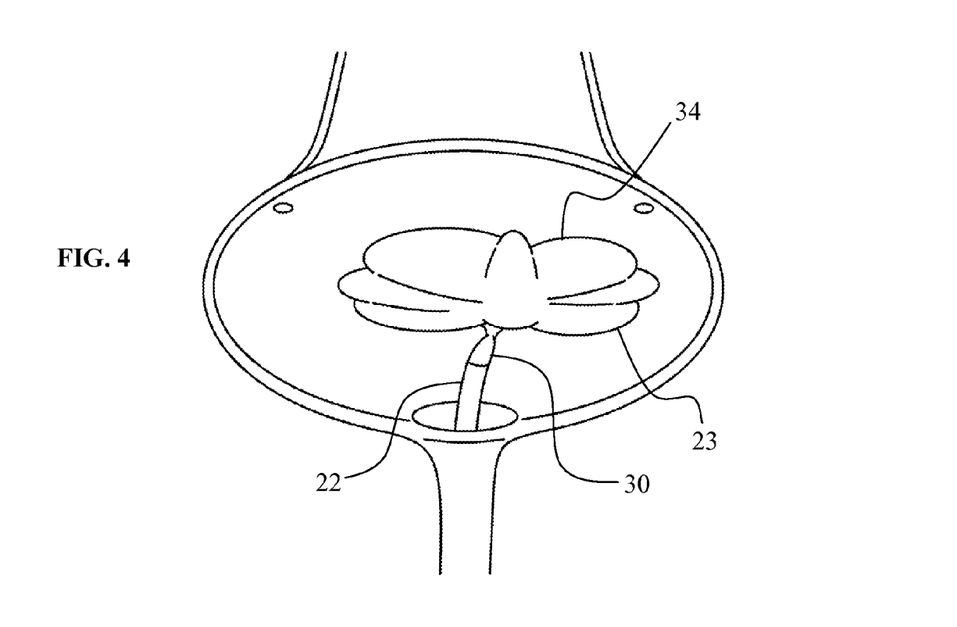
FIG. 4 is a representative cross-sectional side view of a bladder illustrating inflation of a balloon of the drug delivery device depicted in FIG. 3.
Figure 8:
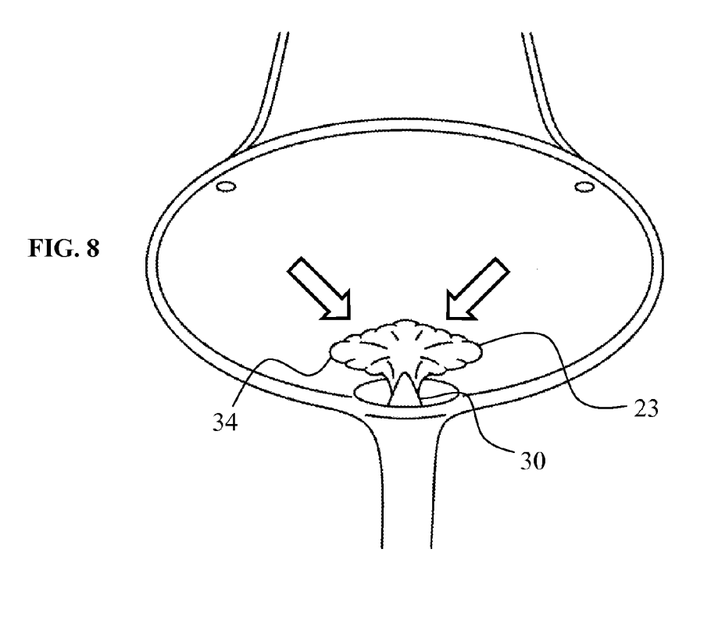
FIG. 8 is a representative cross-sectional side view of a bladder depicting deflation and removable of the balloon depicted in FIG. 3.

As depicted in FIGS. 3-5 and 8, in operation, the catheter 22 is navigated through the urethra such that at least the tip 30 penetrates the urethra sphincter, wherein the balloon 34 is positioned within the tip space 32 in the deflated non-expanded space 23. A quantity of the treatment drug solution is pumped through the lumen 28 into the interior space 38 of the balloon 34 to inflate the balloon 34 and transition the balloon 34 into the inflated expanded state 25 as depicted in FIG. 4. The inflation of the balloon 34 causes the balloon 34 to leave the tip space 32 and continue to expand within the bladder. In one aspect, the balloon 34 is deployed from the tip space 32 with the control wire before the balloon 34 is inflated. After the balloon 34 is inflated, the tip 30 is separated from the balloon 34. In this configuration, the balloon 34 comprises a sealing orifice 42 that maintains the inflation of the balloon 34 as the drug treatment solution is slowly administered through the balloon wall 36. Following treatment, in one aspect, the balloon 34 can be deflated by the tip 30 of a second catheter 22 and drained of the remaining drug treatment solution before the deflated balloon 34 is pulled from the bladder as depicted in FIG. 8.

In one aspect, the balloon walls 36 of the inflated balloon 34 can be sized to be proximate to the bladder walls as shown in FIGS. 5-7. The close proximity of the balloon walls 36 allows for dispensing of the treatment drug solution from the balloon 34 proximate to the bladder walls minimizing the possible dilution of the drug solution by the urine. In one aspect, the catheter 22 can remain attached to the balloon 34 throughout the treatment to provide a continuous supply of the treatment drug solution.

Figure 9:
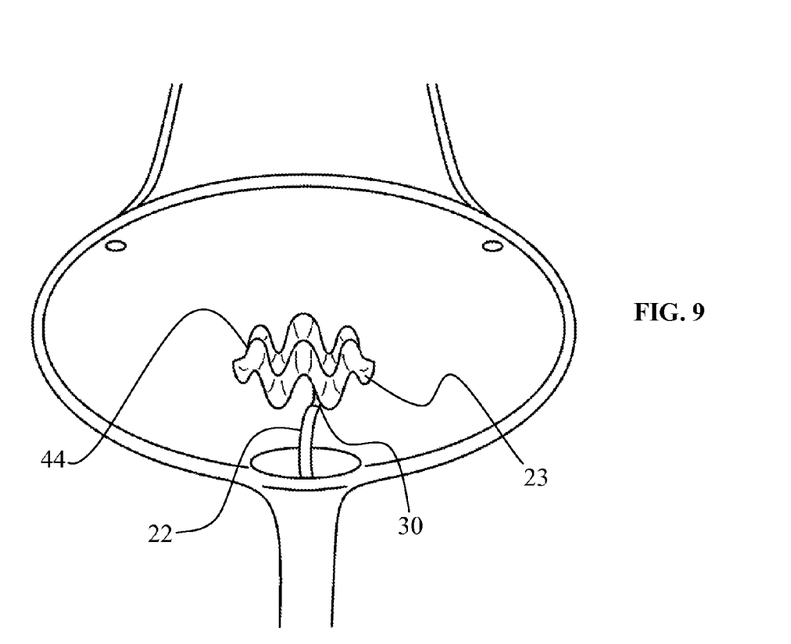
FIG. 9 is a representative cross-sectional side view of a bladder depicting deployment of a ring of a drug delivery device according to an embodiment of the present invention.
Figure 10:
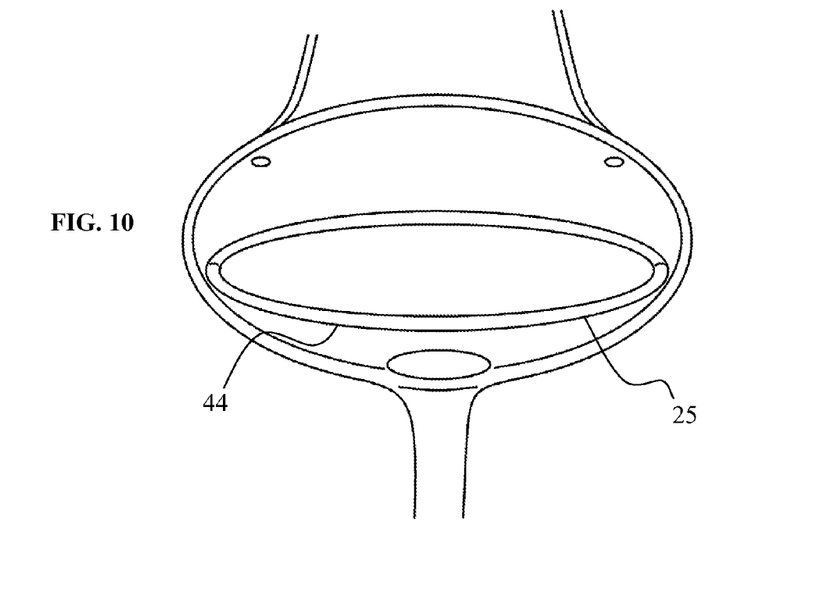
FIG. 10 is a representative cross-sectional side view of a bladder depicting a deployed ring of the drug delivered device depicted in FIG. 9.

As depicted in FIG. 9-10, the deployable delivery element 24 can comprise a collapsible ring 44 having a collapsed non-expanded state 23 and an inflated expanded state 25. In one aspect, the ring 44 can comprise a balloon having an interior space and inflatable by feeding a quantity of treatment drug solution into the ring 44. In another aspect, the ring 44 can comprise a flexible ring 44 biased to expand upon deployment from tip 30. As with the balloon 34, the ring 44 is positioned within the tip space 32 in the non-expanded state 23. After insertion of the tip 30 through the urethral sphincter, the ring 44 is inflated or expanded within the bladder.

In one aspect, the ring 44 comprises a semi-permeable material allowing the treatment drug contained within the ring to diffuse from the ring 44 over a prolonged period of time while preventing urine from entering the interior of the ring 44. In another aspect, the ring 44 comprises a degradable material that gradually breaks down over an extended period of time, thereby gradually dispensing the treatment drug contained within the ring 44. In yet another aspect, the ring 44 can further comprise a plurality of orifices 46 through which the treatment drug solution can be eluted.

Figure 11:
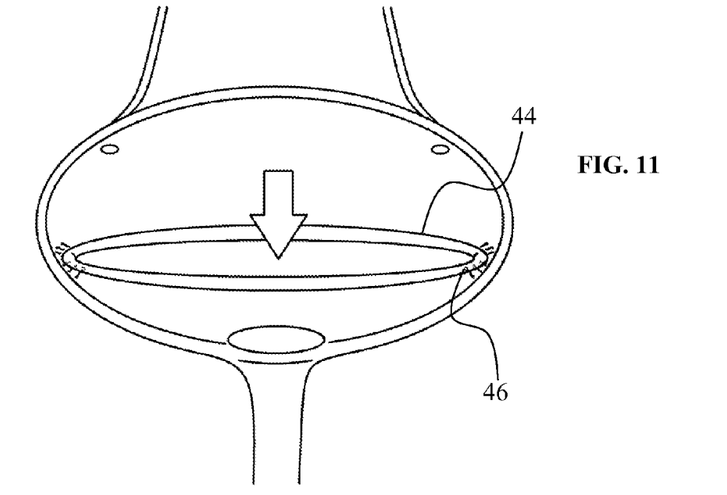
FIG. 11 is a representative cross-sectional side view of a bladder depicting flow of fluid through the bladder and the elution of treatment drugs from the deployed ring depicted in FIG. 10.

As depicted in FIG. 11, in one aspect, the ring 44 is sized such that the outer edge of the ring 44 engages the bladder walls to retain the ring 44 within the bladder. In this configuration, the direct engagement of the ring 44 to the bladder walls allows for direct transfer of treatment drug solution to the bladder walls, thereby minimizing the dilution of the treatment drug solution in the urine. Alternatively, the ring 44 is sized to be too large to be passed through the urethral sphincter. In either configuration, urine can pass normally through the center of the ring 44 and out of the bladder through the urethra, thereby allowing normal bladder functions while administering the treatment drug solution.

As depicted in FIGS. 2-11, a method of a administering a treatment drug solution over an extended period of time from within a bladder comprises navigating a catheter 22 having a tip 30 with a deployable delivery element 24 contained therein, wherein the delivery element 24 is in a non-expanded state 23 when positioned within the catheter tip 30. The method further comprises deploying the delivery element 24 from the tip 30 and expanding the delivery element 24 within the bladder. In one aspect, the method can also comprise transferring a quantity of drug treatment solution through the catheter 22 to expand the delivery element 24 into an expanded state 25. In another aspect, the method can also comprise pushing the delivery element 24 from the catheter tip 30 with a control wire, wherein the delivery element 24 is folded such that the delivery element 24 is biased to transition into the expand state 25 upon exiting the catheter tip 30. The method further comprises diffusing the quantity of treatment drug solution from the delivery element 24 over a period of time. Finally, the method also comprises deflating the delivery element 24 and removing the delivery element 24 from the bladder through the urethra with the catheter 22.

Figure 12:
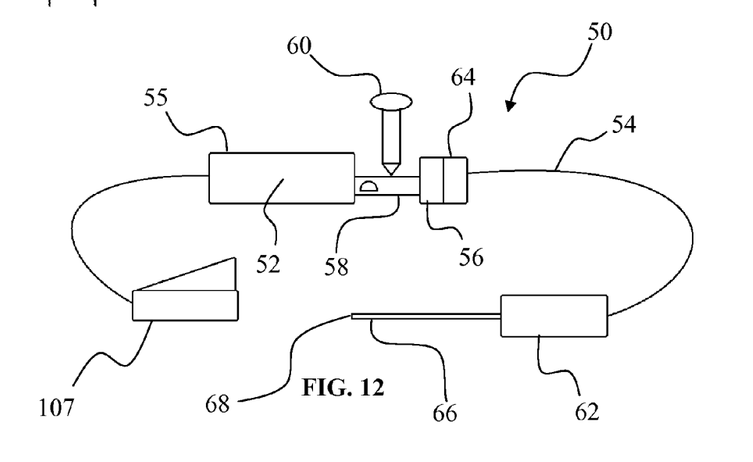
FIG. 12 is a schematic diagram of a drug delivery device with a jet injection system according to an embodiment of the present invention.
Figure 13:
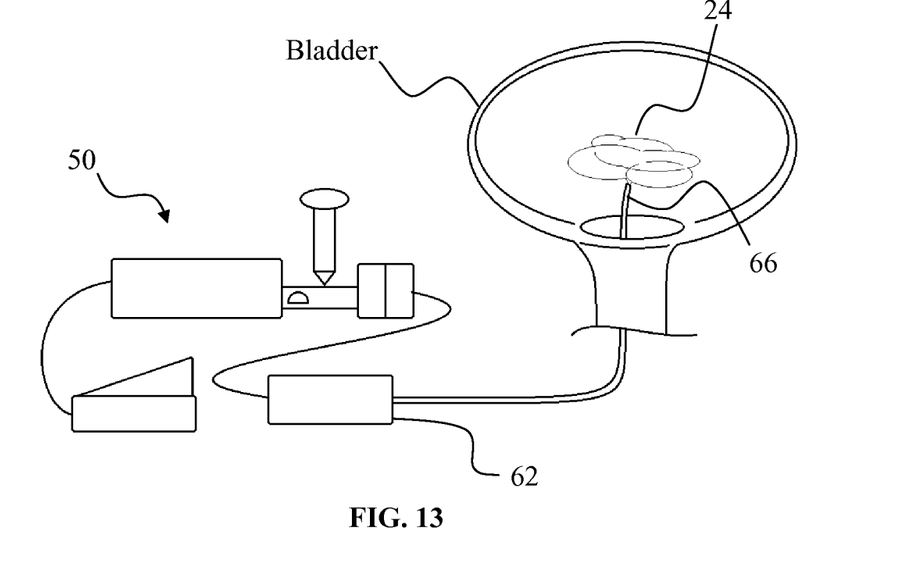
FIG. 13 is a schematic diagram of a drug delivery device with a jet injection system illustrating deployment of a deployable delivery element within a bladder.
Figure 14:
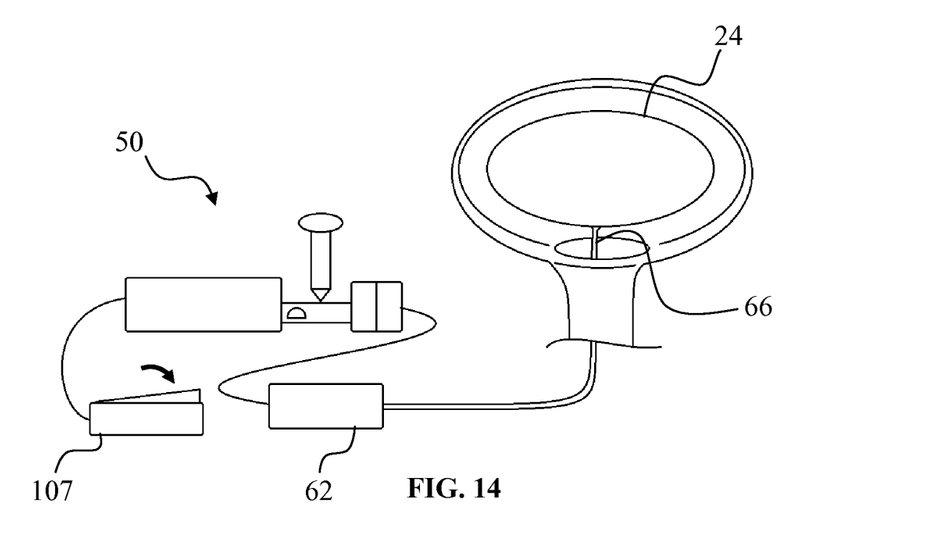
FIG. 14 is a schematic diagram of a drug delivery device with a jet injection system illustrating delivery of treatment drugs from a deployed delivery element.

In an alternative embodiment illustrated within FIGS. 12-14, deployable delivery element 24, for example, balloon 34 or collapsible ring 44 can delivered and placed within the bladder as previously described. Once the deployable delivery element 24 is properly positioned and in expanded state 25, a medical professional can utilize a jet injection system 50 such as, for example, the jet injection systems described in U.S. Patent Publication Nos. 2008/0119784, 2008/0119823, 2009/0312696, 2011/0046600, 2011/0172631, 2011/0015614, 2011/0238006, 2011/0245762, 2011/0264036, 2011/0282318, 2012/0053515, 2012/0109049, 2012/0109050, 2012/0302826 and U.S. Pat. Nos. 7,850,649 and 7,993,264, all publication and patents being incorporated herein by reference, to rapidly deliver the treatment drug solution into the deployable delivery element 24. Correspondingly, the rate at which the drug treatment solution is then administered into the bladder tissue is greatly increased so as to further reduce the potential for dilution and to facilitate treatments where a medical professional desires rapid introduction of the drug treatment solution as opposed to a slower, time delayed delivery of the drug treatment solution.

As illustrated in FIG. 12, jet injection system 50 can comprise an injector 52 and an applicator lumen 54. Injector 52 can comprise an automated injector 55 including a user interface 56 and a connector member 58. Connector member 58 can include a surface opening (not shown) for communication with a drug treatment solution supply 60. User interface 56 can comprise an input means allowing a medical profession to control and selectively deliver pressurized drug treatment solution through the connector member 58 and into the applicator lumen 54. Representative input means can include for example, a foot pedal 107, switches, buttons or a touch-screen capable of receiving touch commands as well as displaying system information including a mode of operation as well as operating parameters.

As seen in FIGS. 13 and 14, applicator lumen 54 preferably comprises a polymeric tubular device 62 having a proximal attachment end 64 and a distal delivery end 66. Polymeric tubular device 62 is generally formed so as to have a burst strength of at least about 2,000 psi. In a preferred embodiment, the non-metal, polymeric tubular device is formed to have a burst strength ranging from about 2,000 psi to about 5,000 psi. In one representative embodiment, non-metal, polymeric tubular device 200 is formed of a single high strength polymer such as, for example, a polyimide, polyetherimide available from General Electric under the trade name Ultem® and linear aromatic polymers such as PEEK™ available from Victrex plc. Alternatively, the non-metal, polymeric tubular device 62 can be formed from a reinforced polymer that is reinforced with reinforcing materials such as, for example, nano-particles, clays or glass. Alternatively, the polymeric tubular device 62 can be reinforced with a reinforcing fiber such as, for example, tubes braided with carbon fiber, synthetic para-aramid fiber such as Kevlar available from E.I. du Pont de Nemours and Company or other high-strength polymers braided within polymeric tubular device 62. Generally, polymeric tubular device 62 is extruded though other appropriate fabrication methods including molding can be utilized as well.

As illustrated in FIG. 12, polymeric tubular device 62 can be configured to be advanced through the catheter 22 following deployment and placement of the deployable delivery element 24. Alternatively, deployable delivery element 24 can be retained within the polymeric tubular device 62 such that the deployable delivery element 24 is positioned and deployed directly out of the applicator lumen 54. With the deployable delivery element 24 positioned and deployed within the bladder, the medical professional can actuate the injector 52 to deliver high pressure drug treatment solution into the deployable delivery element 24 through a delivery orifice 68 at the distal delivery end 66. In this manner, the medical professional can quickly deliver the drug treatment solution into the deployable delivery element 24 at a higher rate and higher pressure for quicker delivery through the deployable delivery element 24 and into the bladder tissue.

While the invention is amenable to various modifications and alternative forms, specifics thereof have been shown by way of example in the drawings and described in detail. It is understood, however, that the intention is not to limit the invention to the particular embodiments described. On the contrary, the intention is to cover all modifications, equivalents, and alternatives falling within the spirit and scope of the invention as defined by the appended claims.

The invention claimed is:

1. A drug delivery device for treating bladder disorders, comprising:
    a first catheter having a lumen defined between a proximal end and a distal tip comprising an inner tip space; and
    a delivery element having a first non-expanded state and a second expanded state,
    wherein the delivery element is fully contained within the inner tip space of the lumen as the distal tip is navigated into a bladder;
    wherein the delivery element transitions to the second expanded state when the delivery element is advanced out of the lumen such that the delivery element contacts an internal bladder wall to deliver a treatment drug from the delivery element to the bladder; and
    wherein the delivery element is separable from the first catheter after the delivery element transitions to the second expanded state.

2. The drug delivery device of claim 1, wherein the delivery element comprises a flexible ring, wherein the flexible ring assumes a folded state in the first non-expanded state and assumes a ring shape when in the expanded state.

3. The drug delivery device of claim 2, wherein the flexible ring comprises a drug eluting flexible ring such that the treatment drug is delivered to the bladder through contact of the drug eluting flexible ring with the internal bladder wall.

4. The drug delivery device of claim 2, wherein the flexible ring allows passage of urine through a center portion of the ring such that the flexible ring can remain in the expanded state within the bladder without impacting bladder function.

5. The drug delivery device of claim 1, wherein the delivery element comprises a first inflation balloon, and wherein the first inflation balloon assumes an uninflated state in the first non-expanded state and assumes an inflated state in the second expanded state.

6. The drug delivery device of claim 5, wherein an exterior balloon wall is in contact with the internal bladder wall when the inflation balloon is in the second expanded state.

7. The drug delivery device of claim 6, wherein the inflation balloon is inflated with an inflation fluid to assume the second expanded state.

8. The drug delivery device of claim 7, wherein the inflation fluid comprises the treatment drug.

9. The drug delivery device of claim 5, wherein the first inflation balloon comprises a semi-permeable membrane.

10. The drug delivery device of claim 5, wherein the first inflation balloon comprises a plurality of orifices formed in a balloon wall.

11. The drug delivery device of claim 10, wherein a pressurized inflation fluid is forced through the plurality of orifices, the pressurized inflation fluid including the treatment drug.

12. The drug delivery device of claim 1, wherein the treatment drug is introduced into the delivery element with a jet injection system.

13. A method for delivering a bladder treatment drug, comprising:
    providing a first catheter having a lumen defined between a proximal end and a distal tip comprising an inner tip space, the first catheter including a delivery element within the inner tip space of the lumen;
    advancing the delivery element out of the lumen and expanding the delivery element so that the delivery element assumes an expanded disposition within a bladder, wherein the delivery element is in contact with an internal bladder wall;
    separating the delivery element from the first catheter within the bladder;
    removing the first catheter from the bladder; and
    delivering a bladder treatment drug to the internal bladder wall through continuing contact of the delivery element with the internal bladder wall.

14. The method of claim 13, wherein the delivery element comprises a foldable ring.

15. The method of claim 14, further comprising:
    allowing urine to pass through a center portion of the foldable ring such that urinary function is maintained following removal of the first catheter.

16. The method of claim 15, further comprising:
    eluting the treatment drug from the flexible ring to the internal bladder wall through continued contact of the flexible ring with the internal bladder wall following removal of the first catheter.

17. The method of claim 13, wherein the delivery element comprises a first inflation balloon, and where the method further comprises:
    inflating the first inflation balloon with an inflation fluid such that the first inflation balloon is in contact with the internal bladder wall.

18. The method of claim 17, wherein the inflation fluid comprises the bladder treatment drug and wherein the expansion of the delivery element and delivery of the bladder treatment drug comprises:

pressurizing the inflation fluid such that the inflation fluid is directed through a plurality of orifices in a wall of the first inflation balloon such that the bladder treatment drug is delivered to the internal bladder wall.

19. The method of claim 13, further comprising:

injecting the bladder treatment drug into the delivery element with a jet injection system.

* * * * *